(12) United States Patent
Smith et al.

(10) Patent No.: US 7,022,093 B2
(45) Date of Patent: Apr. 4, 2006

(54) SELF-CONTAINED HEATING AND COOLING ORTHOPAEDIC BRACE

(75) Inventors: Ira Mark Smith, Marshall, TX (US); Jeffrey Ronald Mottershaw, Marshall, TX (US)

(73) Assignee: Thermodesigns, Inc., Cornelia, GA (US)

( * ) Notice: Subject to any disclaimer, the term of this patent is extended or adjusted under 35 U.S.C. 154(b) by 0 days.

(21) Appl. No.: 10/679,717

(22) Filed: Oct. 6, 2003

(65) Prior Publication Data

US 2005/0075593 A1 Apr. 7, 2005

(51) Int. Cl.
*A61F 5/00* (2006.01)

(52) U.S. Cl. .............................. 602/2; 607/96; 607/114; 602/14

(58) Field of Classification Search ................. 21/529; 128/878, 882; 602/2, 5, 14, 20, 23; 607/96, 607/114
See application file for complete search history.

(56) References Cited

U.S. PATENT DOCUMENTS

| | | | | |
|---|---|---|---|---|
| 4,716,892 A | * | 1/1988 | Brunswick | 602/21 |
| 4,930,317 A | * | 6/1990 | Klein | 62/3.3 |
| 4,964,402 A | * | 10/1990 | Grim et al. | 602/2 |
| 5,169,384 A | * | 12/1992 | Bosniak | 604/20 |
| 5,190,032 A | * | 3/1993 | Zacoi | 128/400 |
| 5,407,421 A | * | 4/1995 | Goldsmith | 602/5 |
| 5,415,624 A | * | 5/1995 | Williams | 602/21 |
| 5,534,021 A | * | 7/1996 | Dvoretzky | 607/112 |
| 5,741,220 A | * | 4/1998 | Brink | 602/14 |
| 5,836,903 A | * | 11/1998 | Peters | 602/27 |
| 6,017,337 A | * | 1/2000 | Pira | 606/20 |
| 6,074,414 A | * | 6/2000 | Haas et al. | 607/108 |
| 6,125,636 A | * | 10/2000 | Taylor et al. | 62/3.5 |
| 6,141,801 A | * | 11/2000 | Helenick | 2/159 |
| 6,375,674 B1 | * | 4/2002 | Carson | 607/104 |
| 6,613,953 B1 | * | 9/2003 | Altura | 602/43 |
| 2002/0143373 A1 | * | 10/2002 | Courtnage et al. | 607/91 |

* cited by examiner

Primary Examiner—Henry Bennett
Assistant Examiner—Dinnatia Doster-Greene
(74) Attorney, Agent, or Firm—Greg O'Bradovich, Esq.; Myers & Kaplan, LLC (57) ABSTRACT

A self-contained heating and cooling orthopaedic brace is described. The brace generally includes a main body having straps to support the brace on the desired area of the body. These areas can include the back, knee, elbow and shoulder. The brace further includes inner pockets having heating and cooling pads connected to a temperature controller that allows manual adjustment of the desired temperature. The heating and cooling elements in the pad typically utilize the Peltier Effect. The temperature controller can include a rechargeable battery for prolonged use. In addition, the brace is a material that allows temperature retention for further prolonged use. The user's own body moisture is also retained for moist heat applications.

11 Claims, 6 Drawing Sheets

Fig_1

Fig_8

Fig_2A

Fig_2B

Fig_2C

Fig_9

SELF-CONTAINED HEATING AND COOLING ORTHOPAEDIC BRACE

BACKGROUND

I. Field of the Invention

The present invention relates generally to the field orthopaedics, and more particularly to orthopaedic braces having a self-contained heating and cooling apparatus and system.

II. Description of the Related Art

Many orthopaedic injuries and conditions require the use of both and orthopaedic brace as well as heating, cooling or alternating heating and cooling. Several different braces are offered for knees, backs and shoulders. For example, several knee braces are looped over the leg and completely surround the knee area, which can often cause binding in the back of the knee when the user bends the knee.

Furthermore, when heating and cooling are required, bulky ice packs, heating bottles and hot/cold gel backs are often used to heat and cool the affected areas. These heating and cooling instruments are often bulky and must be secured with elastic bandages and the like. It is often also difficult to use these heating and cooling instruments in conjunction with braces. Therefore, the user must often be immobile when heating and cooling. When using gel packs, the heating and cooling is often extreme. For cooling, the gel pack is often put in a freezer. For heating, the gel back is typically put in a microwave oven. As such, the cold gel packs can often be initially too cold. The heated gel packs can often initially cause scalding. In addition, the heat and cool can dissipate quickly over time. A further disadvantage is that the heat and cold cannot be manually controlled and adjusted for the present need.

SUMMARY

In general, the invention features a self-contained heating and cooling orthopaedic brace. The brace generally includes a main body having straps to support the brace on the desired area of the body. These areas can include the back, knee, elbow and shoulder. The brace further includes inner pockets having heating and cooling pads connected to a temperature controller. The heating and cooling pads typically include a heating elements, one side of which cools while the other side heats. One side is therefore used to deliver the desired temperature, while the other side is typically used to dissipate the undesired temperature. In a typical implementation, the heating and cooling element is a device that utilized the Peltier Effect. The temperature controller controls the intensity of the desired temperature and can optionally switch between heating and cooling. The temperature controller can include a rechargeable battery for prolonged use. In addition, the brace is a material that allows temperature retention foe further prolonged use. The user's own body moisture is also retained for moist heat applications.

In general, in one aspect, the invention features an orthopaedic brace temperature controlled apparatus, including a temperature element having a first surface and a second surface and a thermally conductive sheet connected to each of the first and second surfaces;

In one implementation, the apparatus further includes a thermally insulating sheet the temperature element being located within the sheet.

In another implementation, the thermally insulating sheet is located between the thermally conductive sheet connected to the first surface and the thermally conductive sheet connected to the second surface.

In another implementation, the apparatus further includes a thermal adhesive located between the first surface and the thermally conductive sheet and between the second surface and the thermally conductive sheet.

In another implementation, the apparatus further includes a temperature controller connected to the temperature element.

In another implementation, the temperature element is a Peltier chip.

In another aspect, the invention features an orthopaedic brace, including a main body having an outer surface, an inner surface and an opening, two elongated primary straps connected to one side of the main body, the primary straps being generally parallel to one another, a secondary strap connected to the end of each of the primary straps, buckles connected to the main body on the outer surface, a first set of primary strap fasteners being connected to the outer surface of the main body adjacent the opening, a second set of primary strap fasteners connected to the end of the primary straps adjacent the connection point of the primary straps and the secondary straps.

In one implementation, the brace further includes a first set of secondary strap connectors located on a surface of each of the secondary straps and a second set of secondary strap connectors located on the same surface and parallel to the first set of secondary strap connectors.

In another implementation, the brace further includes a pocket connected to the inner surface of the main body adjacent the opening.

In another implementation, the pocket includes a front panel and a rear panel, the rear panel being connected to the inner surface of the main body.

In another implementation, the front panel is mesh.

In another implementation, the brace further includes a temperature pad.

In still another implementation, the temperature pad includes a temperature element having a first surface and a second surface, a thermally conductive sheet connected to each of the first and second surfaces, a thermally insulating sheet located between the thermally conductive sheets, the temperature element being located within the sheet and thermal adhesive located between the first surface and the thermally conductive sheet and between the second surface and the thermally conductive sheet.

In yet another implementation, the brace further includes a temperature controller connected to the temperature element.

In another aspect, the invention features a back brace including a main body having an inner and outer surface, straps connected to either side of the main body and a spinal cushion connected to the inner surface of the main body.

In one implementation, the main body includes an inner panel and an outer panel.

In another implementation, the brace further includes a pocket connected to the inner surface of the main body and adjacent the spinal cushion.

In another implementation, the pocket comprises a rear panel connected to the inner surface of the main body and an outer panel connected to the rear panel.

In another implementation, the brace further includes a temperature pad located within the pocket.

In another implementation, the brace further includes a temperature controller connected to the temperature pad.

In yet another aspect, the invention features an orthopaedic brace, including a main body having an inner and outer surface, straps connected to the main body, a pocket connected to the inner surface of the main body and a temperature pad located within the pocket.

In still another aspect, the invention features a self-contained heating and cooling orthopaedic kit, including an orthopaedic brace including a main body having an inner and outer surface, straps connected to the main body, a pocket connected to the inner surface of the main body and a temperature pad located within the pocket, a temperature controller connected to the temperature pad, the controller being adapted to deliver power to control the intensity of the temperature, a rechargeable battery adapted to be placed in the temperature controller to provide power to the temperature controller and a rechargeable battery unit adapted to receive the battery to recharge the battery.

In another aspect, the invention features an orthopaedic brace temperature control circuit, including a first temperature element having a first surface and a second surface, a second temperature element having a first surface and a second surface and a transistor connected to a voltage divider for supplying voltage to the temperature elements.

In one implementation, the circuit further includes a third temperature element having a first surface and a second surface and a fourth temperature element having a first surface and a second surface, wherein the first surfaces of third and fourth temperature elements are thermally coupled to the second sides of the first and second temperature elements.

In another implementation, the circuit further includes a diode connected between the first and the second temperature elements and the third and fourth temperature elements.

One advantage of the invention is that it provides the user with total mobility while delivering temperature therapy.

Another advantage of the invention is that the temperature delivery system does not have to be externally heated and cooled.

Another advantage of the invention is that the desired temperature does not dissipate quickly over time but provides prolonged consistent temperatures.

Another advantage of the invention is that the degree of temperature can be manually adjusted and responds quickly.

Another advantage of the invention is that the temperature controller power can be cut off to conserve power.

Another advantage is that the power source can be easily recharged in the home or in an automobile.

Other objects, advantages and capabilities of the invention will become apparent from the following description taken in conjunction with the accompanying drawings showing the preferred embodiment of the invention.

DETAILED DESCRIPTION

Figure 1:
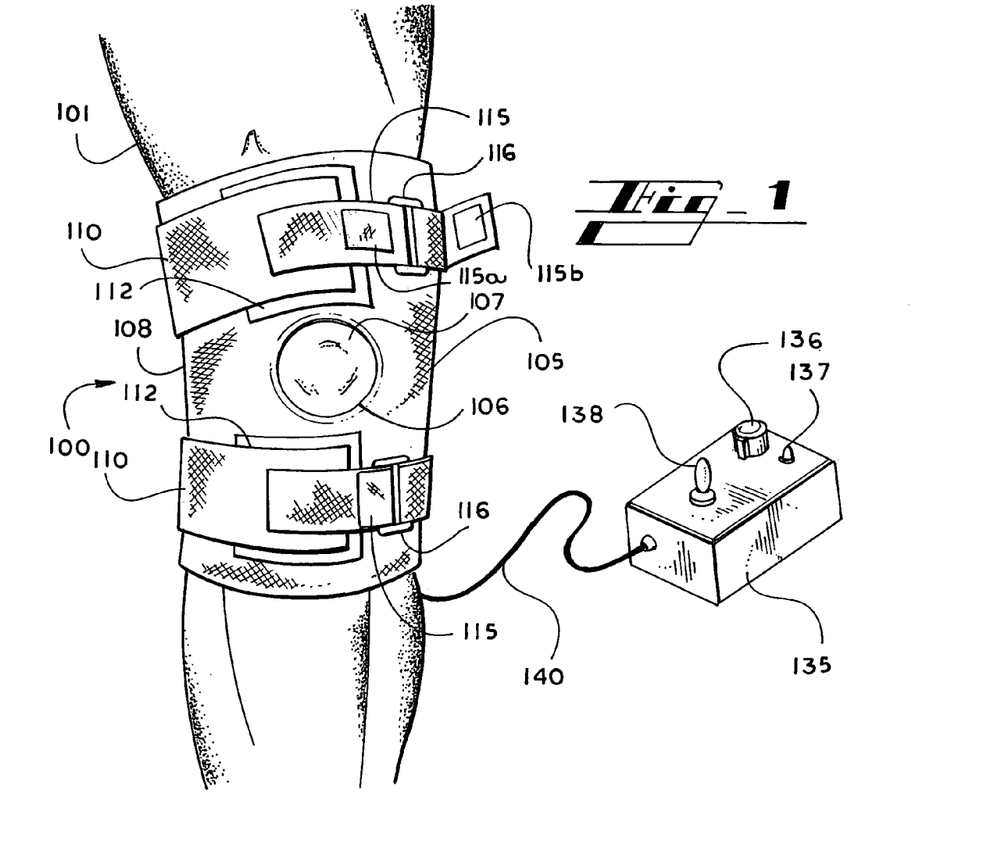
FIG. 1 illustrates an embodiment of a self-contained heating and cooling knee brace on a user's leg.

Referring to the drawings wherein like reference numerals designate corresponding parts throughout the several figures, reference is made first to FIG. 1 that illustrates an embodiment of a self-contained heating and cooling knee brace 100 on a user's leg 101. As is better appreciated below, other embodiments of the brace 100 can be dimensionally modified to affix to a user's elbow.

The brace 100 generally includes a main body 105 having an opening 106 that exposes and cradles the user's patella 107. The main body 105 generally includes an inner surface in contact with the user and an outer surface. In general, as described further below with respect to FIG. 2, the brace 100 includes a dual-strapping system that includes two sets of straps, primary straps 110 and secondary straps 115 that interact with each other and with the main body 105 to provide a snug and secure fit around the user's leg 101. Furthermore, because the primary straps 110 wrap around the user's leg 101 in a separated and parallel manner, a spacing 108 (see FIG. 2) is left in between the straps 110 thereby providing a space in the back of the user's knee. This space 108 prevents binding that often occurs with a conventional brace that surrounds the user's entire knee and leg. In a typical embodiment, the main body 105 and the primary straps 110 are in contact with the body and are therefore are soft and comfortable, but also insulating (to retain the heat and cool on the desired body area) and flexible. In a typical implementation, the main body 105 and the primary straps 110 are neoprene although other suitable brace materials are contemplated.

The brace 100 further includes buckles 116 that receive and redirect the secondary straps 115 as described in further detail below with respect to FIGS. 2–2C. In general, the primary straps 110 are connected to the main body by a first set of fasteners (111 in FIG. 2 below) that mates with a corresponding set of fasteners 112 that are connected to the main body 105 adjacent the opening 106. In a typical embodiment, the sets of fasteners 111, 112 are hook and loop fasteners. Furthermore, the secondary straps 115 also include two sets of fasteners 115a, 115b on the surface of the secondary straps 115 illustrated in the figure. The sets of fasteners 115a, 115b are generally parallel and adjacent to one another and are adapted to mate and connect to each other as shown in the lower secondary strap 115 in the figure. The upper secondary strap 115 in the figure is illustrated as open exposing both sets of fasteners 115a, 115b. As mentioned above and described in further detail below, the buckles 116 receive and redirect the secondary straps 115 so that the two sets of fasteners 115a, 115b can mate with one another. In a typical embodiment, one of the sets of fasteners 115a, 115b is loop type fasteners and the other set is hook type fasteners.

The brace 100 further includes a temperature controller 135 that is connected to heating and cooling pads (see FIG. 2 below) on the brace 100. The temperature controller 135 is connected to the brace 100 through wiring 140. The temperature controller 135 can be worn by the user, for example, on a belt or in the use's pocket, and be used to provide heating and cooling to the user's knee area as needed. The temperature controller 135 includes a main knob 136 that can be used to turn the controller 135 on and off as well as provide a range of both heat and cold. An indicator 137 provides an intensity of light that is proportional to the level of heat or cold being provided to the knee. In a typical embodiment, the indicator 137 is a light emitting diode (LED). The temperature controller 135 can further include a two-position switch 138 that can be flipped to alternate between heat and cool temperature delivery to the knee.

Figures 2, 3, 3A:
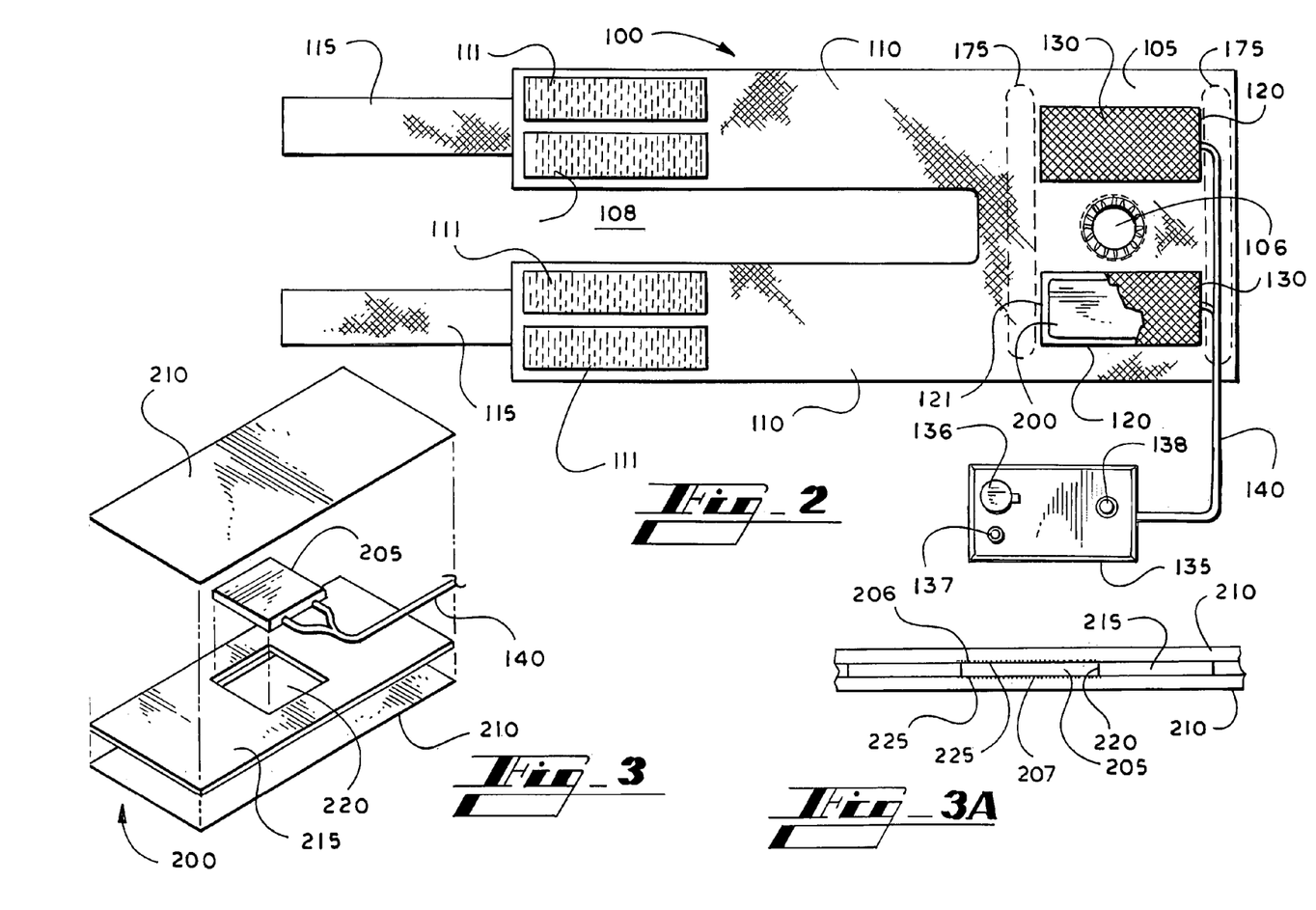
FIG. 2 illustrates an inside view of an embodiment of a self-contained heating and cooling knee brace.
FIG. 3 illustrates a perspective view of the constituent parts of an embodiment of a heating and cooling pad.
FIG. 3A illustrates a side view of the constituent parts of an embodiment of a heating and cooling pad.

FIG. 2 illustrates an inside view of an embodiment of a self-contained heating and cooling knee brace 100. The inside view of the brace 100 illustrates further detail of the brace 100 and the heating and cooling system, which includes the temperature controller 135 and a heating and cooling pad 200 in the brace 100.

In general, the primary straps 110 are connected to one side of the main body 105 and protrude outwards generally parallel to one another. The secondary straps 115 are each connected to a respective end of the primary straps 110 and are generally parallel to each other. As described above the parallel orientation of the primary straps 110 provides a space 108 between the straps 110 thereby preventing binding of the brace 100 when a user bends his knee. The primary straps 110 further include a set of fasteners 111 adjacent to the connection of the primary straps 110 and secondary straps 115. The corresponding set of fasteners 112 is on the reverse surface of the main body 105 adjacent the opening 106, as is described above with respect to FIG. 1 and further below with respect to FIGS. 2A–2C. In addition, as described above with respect to FIG. 1 and as described further below, with respect to FIGS. 2A–2C, the secondary straps 115 include sets of fasteners 115a, 115b on the surface of the secondary straps opposite to the surface shown in FIG. 2.

In another embodiment, the brace 100 can include side supports 175 to provide lateral support typically for ligament support. In a typical embodiment, the side supports can be steel rods.

The brace 100 further includes pockets 120 located generally near the opening 106 for the user's patella 107. The pads 200 are located within the pockets 120. The pockets 120 each generally include a rear panel 121 connected to the main body 105 and a front panel 130 connected to the rear panel 121. In another embodiment, the pocket 120 can include just a front panel 130 connected directly to the main body 105 without the need for a rear panel 121 to form the pockets 120. It is understood that there are various ways that the pockets 120 can be formed. It is understood that the pockets 120 are used to hold and support the pads 200. In general, the front panel 130 must be thin to allow heat and cool to flow freely through it. In a typical embodiment, the front panel 130 is mesh.

The positioning of the pockets 120 determines where the heating and cooling pads 200 are placed relative to the knee. It has been determined that it is generally desirable to deliver heat and cold above and below the knee to treat various knee ailments. However, it is understood that the pockets 120 and therefore the pads 200 can be placed at various other locations on the brace 100 as needed or desired. FIG. 2 further illustrates that the wire 140 branches to both pockets 120 are therefore both pads 200, which is described further below with respect to FIGS. 3 and 3A.

As the user dons and doffs the brace 100, the dual-strapping system allows the brace 100 the be securely fitted around the user's leg and knee for general support as well as good thermal contact for heating and cooling. The general steps for donning the brace 100 are now described with respect to the following figures.

Figure 2A:
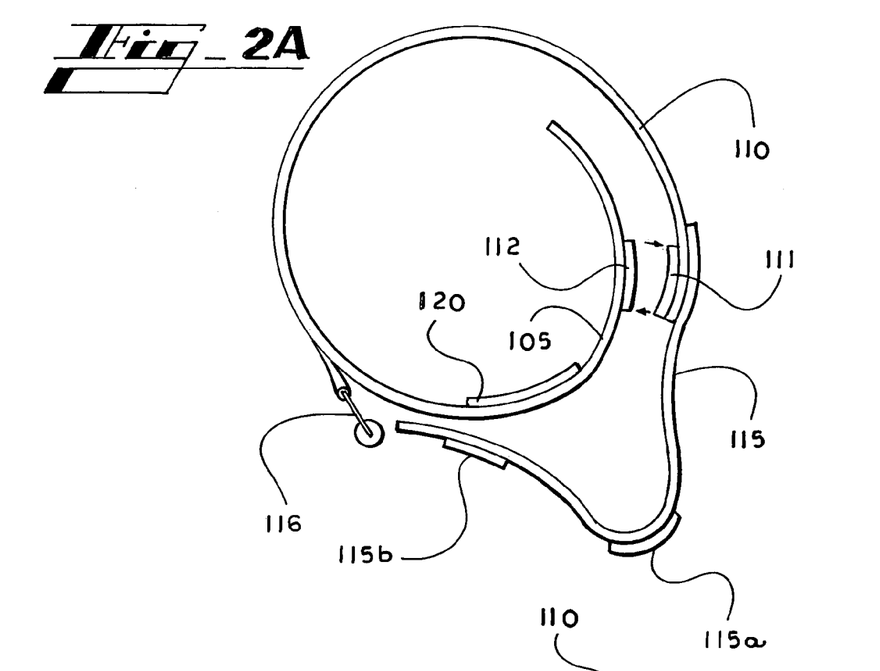
FIG. 2A illustrates a first top down view of an embodiment of a self-contained heating and cooling knee brace in a first orientation.

FIG. 2A illustrates a first top down view of an embodiment of a self-contained heating and cooling knee brace 100 in a first orientation. The top down view allows the features of the dual strapping system to be illustrated. In this first orientation, the user places the brace in the desired location with the patella 107 fit into the opening 106, therefore positioning the pads 200 above and below the patella 107. The brace 100 is encircled around the user's leg and the user can then easily align the sets of fasteners 111, 112 on the primary straps 110 and the main body 105. At this point in the fitting, the secondary strap 115 and the buckle 116 are typically not used. Instead, a desired fitting of the primary straps 110 and the main body 105 is achieved. The user can make several iterations adjusting the upper and lower primary straps 110 as needed to obtain a comfortable fit.

Figure 2B:
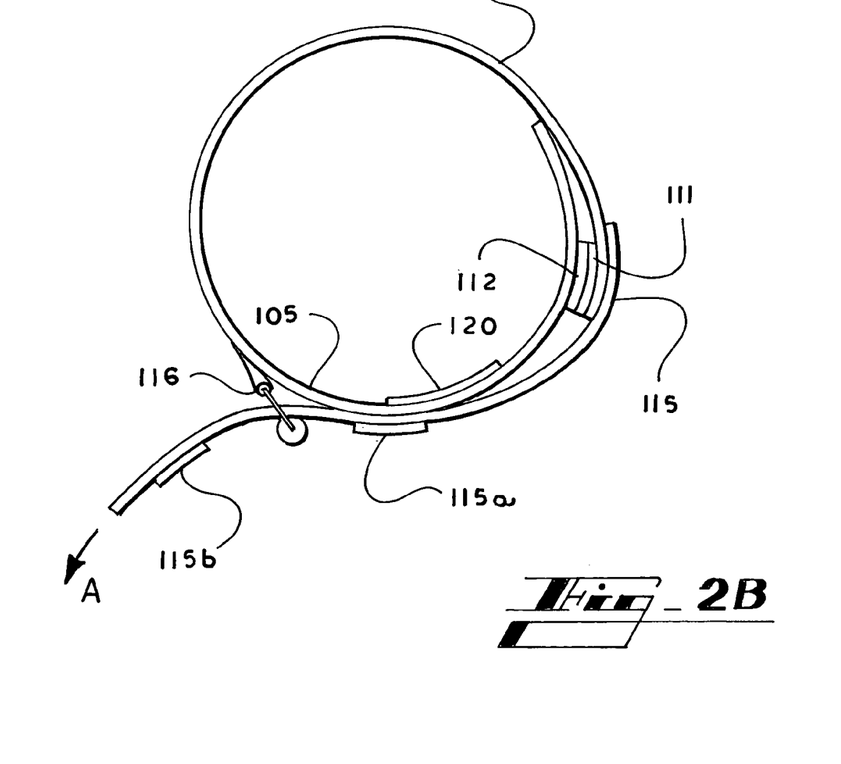
FIG. 2B illustrates a second top down view of an embodiment of a self-contained heating and cooling knee brace in a second orientation.

FIG. 2B illustrates a second top down view of an embodiment of a self-contained heating and cooling knee brace 100 in a second orientation. In this orientation, the user has typically obtained the desired fit of the primary straps 110 and the main body 105 that are connected together by the sets of fasteners 111, 112. In order to obtain and even more secure and comfortable fit to obtain even better thermal contact of the pads 200 (in the pockets 120), the user can then engage the secondary straps 115 of the dual strapping system. The secondary straps 115 are looped through the buckle 116 and pulled and redirected as desired in the direction of arrow A. By pulling on the secondary straps 115, the user can obtain "fine tuning" of the pressure or tightness of the brace 100 on the leg. When the desired fit is obtained, the user then folds the secondary straps 115 onto themselves respectively, to engage the sets of fasteners 115a, 115b.

Figure 2C:
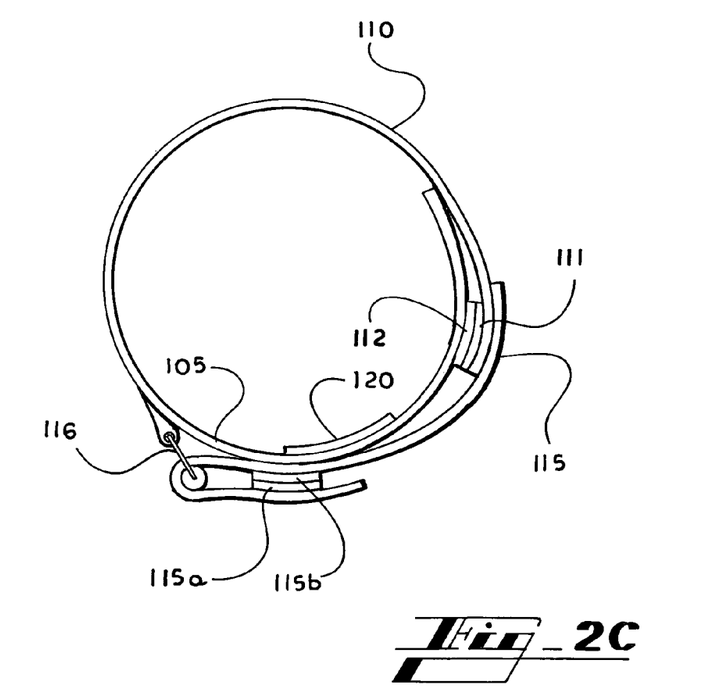
FIG. 2C illustrates a third top down view of an embodiment of a self-contained heating and cooling knee brace in a third orientation.

FIG. 2C illustrates a third top down view of an embodiment of a self-contained heating and cooling knee brace 100 in a third orientation. In this orientation, the primary straps 110 have been secured by fasteners 111, 112 and the secondary straps 115 have been secured by fasteners 115a, 115b. It is appreciated that once the brace is initially placed as described with respect to FIG. 2A, all of the necessary adjustments of the primary and secondary straps are done in the front of the leg adjacent the opening 106 making adjustments of the brace 100 easy and intuitive.

Once the brace 100 is fit as desired, the user can then adjust the heating and cooling as desired. The details of the pad 200 are now described in further detail.

FIG. 3 illustrates a perspective view of the constituent parts of an embodiment of a heating and cooling pad 200. As described above, the pads 200 form a portion of the heating and cooling system of the brace 100. The central component of the pad 200 is a heating and cooling ("temperature") element 205. The element 205 typically provides the ability to deliver both heat and cold. In a typical embodiment, the element 205 is a device that utilizes the Peltier Effect, in which two unlike metals (conductors) in contact with each other produce heating on one side of the device and cooling on the other side of the device. In general, the Peltier Effect is a part of thermoelectric technology. Typically, a Peltier Chip can be used in which two unlike metals are sandwiched between two surfaces (typically ceramic). One surface becomes cold and one surface becomes hot when a current is driven through the metals. In essence, through the Peltier Effect, heat is absorbed on the side that becomes cold and heat is released on the side that becomes hot. Peltier chips are commonly used by those skilled in the computer arts. In the computer arts, the cooling side of Peltier chips are affixed to computer chips, typically in implementations of over-clocking in which the computer chips can become over-heated. The cooling side of peltier chips can be used to lower the temperature of over-clocked ocmputer chips, thereby preventing breakdown of the computer chips.

In general, the descriptions herein discuss that the element 205 and the rest of the pad 200 is used to deliver heat and cold. In the thermally related sciences, it is understood that it is actually heat that is generated dissipated and otherwise delivered. Heat can be said to be pumped from the side that becomes cold to the side that becomes hot. Cold is actually the absence of heat. For purposes of the discussion herein, it is useful to discuss heat and cold delivery for therapeutic purposes. Therefore, thermal delivery refers to both the delivery of heat and cold.

Referring still to FIG. 3, the pads 200 further include strips 210 connected to either side of the element 205. The strips 210 are respectively connected to the hot and cold surfaces of the element 205 in order to deliver the heat and cold to the desired areas. A thermally insulating layer 215 is sandwiched between the two strips 210. The layer 215 includes a hole 220 into which the element 205 is placed. The layer 215 provides thermal isolation between the strips 210, one of which is heated by one surface of the element 205, the other which is cooled by the other surface of the element 205. In a typical embodiment, the layer 215 is closed cell foam that typically provides good thermal insulation, but is also flexible to withstand the movement and bending of the user's knee and leg 101.

It is appreciated that the element 205 used in conjunction with the strips 210 allow rapid and uniform temperature delivery to the desired areas.

As is appreciated in FIG. 2, the pads 200 are in a fixed position in the pockets 120. Therefore, only one of the strips 210 faces the front panel 130 and is therefore the only strip 210 capable of heat and cold delivery. This strip 210 therefore is used to deliver (and dissipate) the heat or cold from the element 205 to the knee and the leg areas. The other strip 210 faces the rear panel 121 and therefore delivers the heat or cold in a direction away from the user and therefore typically does not contribute to any heat and cold delivery. This other strip 210 therefore only serves to dissipate either the heat or cold from the surface of the element.

In the discussion with respect to FIG. 1 above, the temperature controller 135 includes a switch 138 to alternate between heat and cool delivery. It is now better understood that the switch 138 operates to switch the polarity of the current delivered to the element 205, which in turn changes the side of the element 205 that heats and cools. If the patient desires to heat the area, the patient flips the switch 138 to choose the surface of the element 205 facing the patient to heat and the respective strip 210 heats the desired area. The other side of the element 205 therefore cools and the respective strip 210 dissipates the cool. The insulating layer 215 prevents the hot and cold sides from thermally mixing and interfering with the desired heating. Conversely, if the patient desires to cool the area, the patient flips the switch 138 to choose the surface of the element 205 facing the patient to cool and the respective strip 210 cools the desired area. The other side of the element 205 therefore heats and the respective strip 210 dissipates the heat. The insulating layer 215 prevents the hot and cold sides from thermally mixing and interfering with the desired heating.

Typically, the strips 210 are good thermal conductors. In a typical embodiment, the strips 210 are metal sheets or mesh such as copper or aluminum. It is understood that any suitable thermally conducting material can be used for the strips 210. The strips 210 typically also need to be flexible because they are deformed and bent while in the pockets 120 as the user moves his leg and bends his knee.

Referring again to FIG. 1, it is described above that portions of the brace 100 are typically neoprene or other suitable materials. Since it is desired to thermally isolate the desired area of the knee and leg, once the pad 200 is used to heat or cool the area, the thermal insulation of the brace 100 allows the desired are to stay heated or cooled for prolonged periods.

FIG. 3A illustrates a side view of the constituent parts of an embodiment of a heating and cooling pad 200 in an assembled state. As described above, the central component of the pad 200 is the heating and cooling element 205 that is fit into a hole 220 in the thermally insulating layer 215. The two thermally conducting strips 210 are connected to opposite surfaces 206, 207 of the element 205. A thermal adhesive 225 is used to connect the strips 210 to their respective surfaces 206, 206 of the element 205. The thermal adhesive 225 allows a good bond to keep the strips 210 connected to the element while allowing thermal conductivity to still occur between the surfaces 206, 207 and the strips 210. The thermal adhesive 225 also allows the strips 210 to withstand movement and bending while stying attached to the element 205 and conducting the heat and cold from the element 205.

Figures 4, 5:
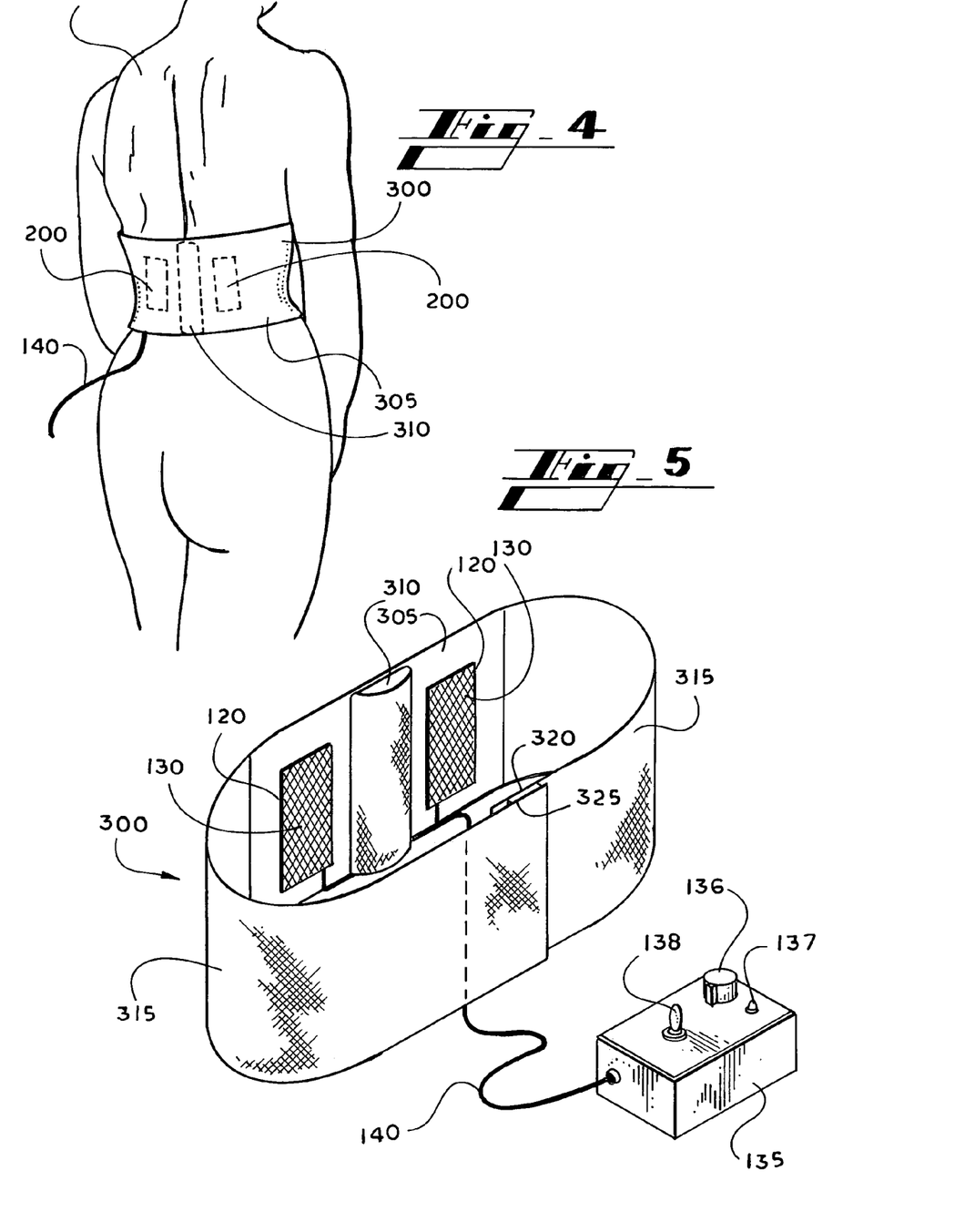
FIG. 4 illustrates an embodiment of a self-contained heating and cooling back brace on a user's back.
FIG. 5 illustrates a perspective view of an embodiment of a self-contained heating and cooling back brace.

FIG. 4 illustrates an embodiment of a self-contained heating and cooling back brace 300 on a user's back 301. The brace 300 generally includes a main body 305 having one or more heating and cooling pads 200 as well as a central spinal cushion 310. The main body 305 generally includes an inner surface in contact with the user and an outer surface. The cushion 310 generally fits on the user's spine to provide comfort and support when the brace 300 is donned. The cushion 310 provides light pressure on the spine and increased thermal insulation. The pads 200 are similar to the embodiments of the pads 200 described above with respect to the knee and elbow brace 100. The pads 200 are electrically coupled to a temperature controller (135 as described above) through wiring 140. The brace 300 is adapted to fit a user's back 301 generally in the lumbar area. It is understood that the brace 300 can be appropriately modified to fit on other areas of the user's back 301.

FIG. 5 illustrates a perspective view of an embodiment of a self-contained heating and cooling back brace 300. As described above, the brace 300 includes the main body 305 and a cushion 310 connected to the main body 305 in a generally vertical manner. On both sides and adjacent the cushion 310, the brace 300 further includes pockets 120 that contain the pads 200 as described further below. Similar to the knee and elbow brace 100 embodiments as described above, the pockets 120 include a front panel 130, which is generally thin and typically mesh to allow heat and cool transfer.

The brace 300 further includes side straps 315 that are respectively connected to the sides of the main body 305. The main body 305 and the straps 315 maybe separate pieces connected together or an integral single piece. In a typical embodiment, the main body 305 and the straps 315 are in contact with the body and are therefore are soft and comfortable, but also insulating (to retain the heat and cool on the desired body area) and flexible. In a typical implementation, the main body 305 and the straps 315 are neoprene although other suitable brace materials are contemplated. Each end of the straps 315 include a set of fasteners 320, 325 respectively. The fasteners 320, 325 are adapted to mate and connect in order to secure the brace 300 around the user's waist and back. In a typical embodiment, the respective straps 320, 325 are hook and loop fastener, although it is understood that other types of fasteners are contemplated, including but not limited to buckles, snaps and the like. The fasteners 320, 325 as used in an overlapping manner help to prevent pinching of the skin in the user's waist area.

The brace 300 further includes a temperature controller 135 that is connected to heating and cooling pads 200. The temperature controller 135 is connected to the brace 300 through wiring 140. The temperature controller 135 can be worn by the user, for example, on a belt or in the use's pocket or on the brace 300 itself, and be used to provide heating and cooling to the user's back area as needed. The temperature controller 135 includes a main knob 136 that can be used to turn the controller 135 on and off as well as provide a range of both heat and cold. An indicator 137 provides an intensity of light that is proportional to the level of heat or cold being provided to the back. In a typical embodiment, the indicator 137 is a light emitting diode (LED). The temperature controller 135 can further include a two-position switch 138 that can be flipped to alternate between heat and cool temperature delivery to the back.

Figures 6, 7:
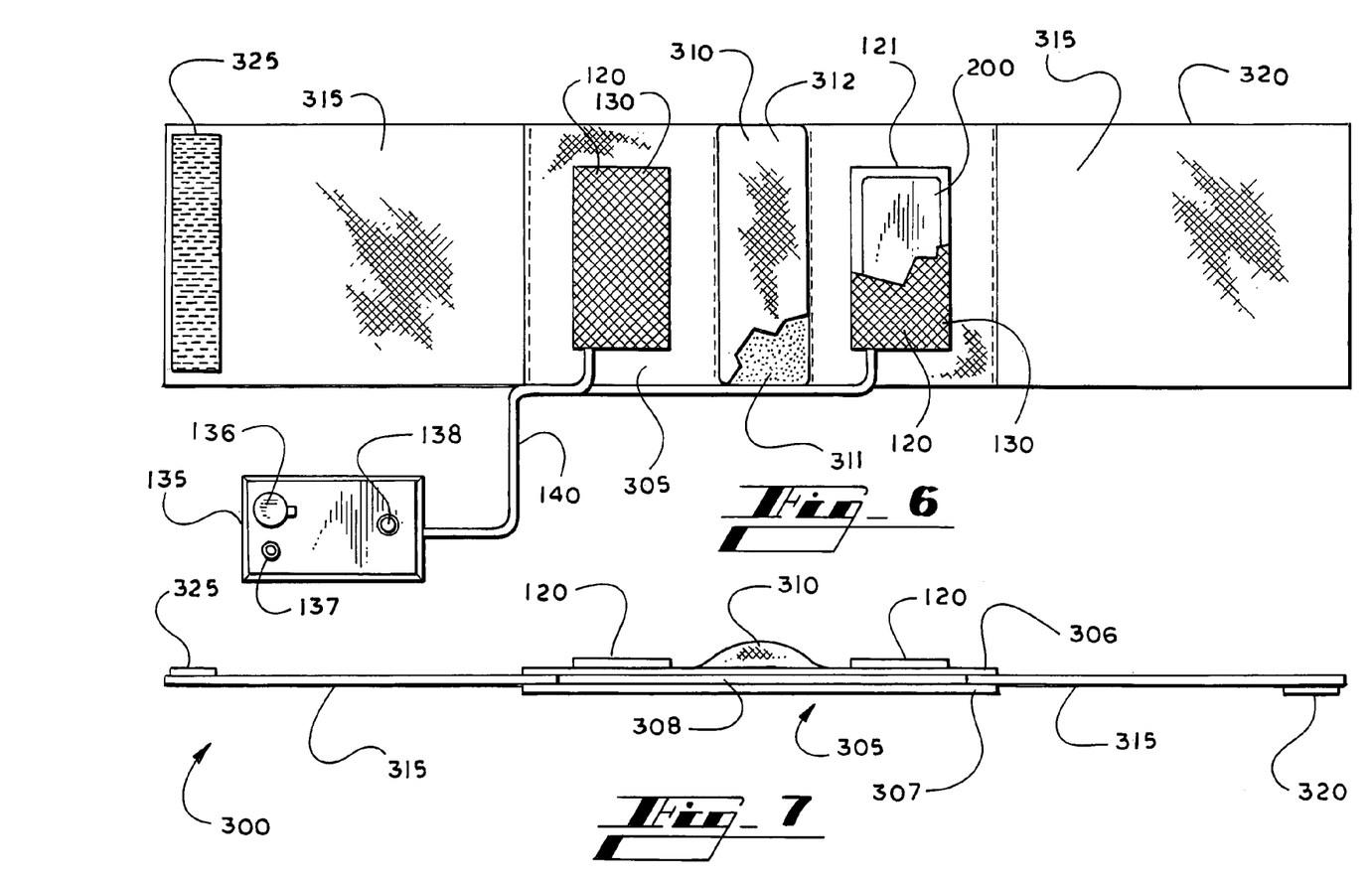
FIG. 6 illustrates an inside view of an embodiment of a self-contained heating and cooling back brace
FIG. 7 illustrates a side view of an embodiment of a self-contained heating and cooling back brace.

FIG. 6 illustrates an inside view of an embodiment of a self-contained heating and cooling back brace 300. In general, straps 315 are connected to either side of the main body 305 and protrude outwards. The straps 315 further include respective sets of fasteners 320, 325 on the ends of the straps 315. The corresponding set of fasteners 112 is on the reverse surface of the main body 105.

The brace further includes the spinal cushions 310 which can include an outer cover 312 and inner padding 311. The brace 300 further includes pockets 120 located generally adjacent and parallel to the cushion 310. The pads 200 are located within the pockets 120. The pockets 120 each generally include a rear panel 121 connected to the main body 305 and a front panel 130 connected to the rear panel 121. In another embodiment, the pocket 120 can include just a front panel 130 connected directly to the main body 305 without the need for a rear panel 121 to form the pockets 120. It is understood that there are various ways that the pockets 120 can be formed. It is understood that the pockets 120 are used to hold and support the pads 200.

The positioning of the pockets 120 determines where the heating and cooling pads 200 are placed relative to the desired are of the back. It has been determined that it is generally desirable to deliver heat and cold on either side of the spine to treat various back ailments. However, it is understood that the pockets 120 and therefore the pads 200 can be placed at various other locations on the brace 100 as needed or desired. FIG. 6 further illustrates that the wire 140 branches to both pockets 120 are therefore both pads 200. In a typical embodiment, the pads 200 are the same pads 200 as described above with respect to FIGS. 3 and 3A.

As the user dons and doffs the brace 300, the straps 315 allow the brace 300 the be securely fitted around the user's waist and back for general support as well as good thermal contact for heating and cooling.

FIG. 7 illustrates a side view of an embodiment of a self-contained heating and cooling back brace 300. This side view figure shows further detail of the brace 300. As described above, the brace 300 includes a main body 305 and two straps 315. The straps 315 include respective fasteners 320, 325 in an opposite orientation so that they can meet and connect when the brace 300 is donned. The brace further includes the spinal cushion 310 and adjacent pockets 120 containing the heating and cooling pads 200 as described above. The figure illustrates that the main body 305 can include and inner and outer panel 306, 307, the ends of which sandwich and connect the respective ends of the straps 315. A further panel 308 can be located between the inner and outer panels 306, 307. In another embodiment, the inner panel 308 can simply be an air space. The main body 305 therefore provides increased thermal insulation in the lumbar area when using several panels.

Figure 8:
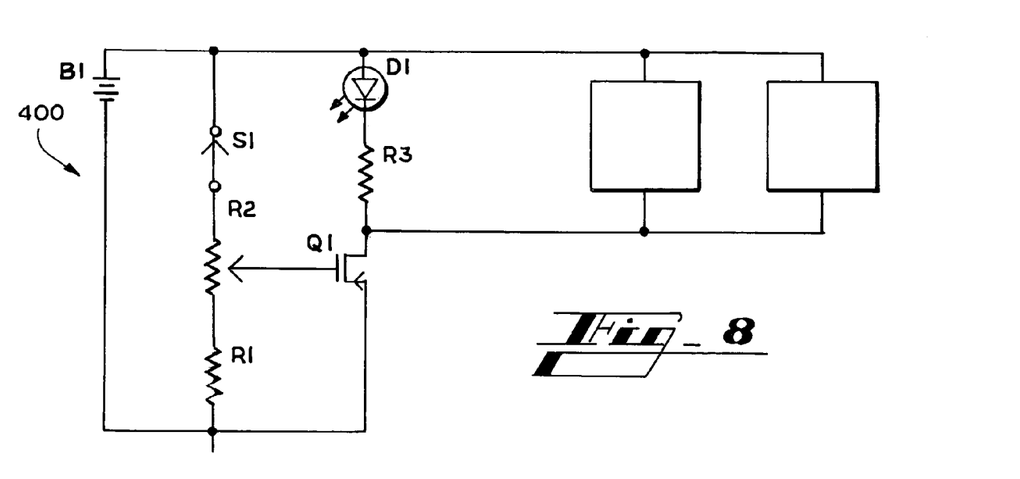
FIG. 8 illustrates a schematic diagram of an embodiment of control circuit.

FIG. 8 illustrates a schematic diagram of an embodiment of a control circuit 400. The control circuit 400 is located within the temperature controller 135 and is used in order to supply power to the pads 200 for heating and cooling. Typically, the circuit 400 is used for implementations in which the embodiments of the braces described above are used for heating or cooling. Therefore, no switch is shown in the circuit 400. The power supplied to the pads 200 determines the intensity of the heating and cooling as described above. The circuit 400 is essentially a voltage controlling circuit to adjust the intensity of the heat or lack of heat of the Peltier chips. Battery B1 is the power source, which in a typical implementation is a lithium-ion battery. Switch S1 is an on/off switch. Resistors R1 and R2 make up a voltage divider controlling gate voltage on transistor Q1, which is typically a power MOSFET that controls the voltage to the Peltier chips. Resistor R3 and diode D1 are parallel to the output and indicate the output voltage intensity.

In cases when it may be difficult to properly cool a desired area because the hot side of the pad 200 as described above is too intense, thereby making it difficult to thermally isolate the cold side of the pad, other embodiments are contemplated. To cool the desired area, additional Peltier chips can be added to the strips of the existing Peltier Chips, typically with the thermal adhesive. The newly added Peltier chips are not turned on during the heating process, but when the toggle switch is changed to cool the area, the newly added Peltier chips would be activated. In the cooling position, the current to a circuit is reversed to the old Peltier Chips and current flows to the newly added Peltier chips. The cold side of the old Peltier chips are toward the desired area of the user and the hot side is outward away from the user. The cold side of the newly added Peltier chips are toward the user and the hot side is facing away from the user. The newly added Peltier chips thus absorb the heat from the old Peltier chips and transfer the heat the hot side of the newly added Peltier chips. Strips can be added to the hot side of the newly added Peltier chips in order to dissipate the heat.

Figure 9:
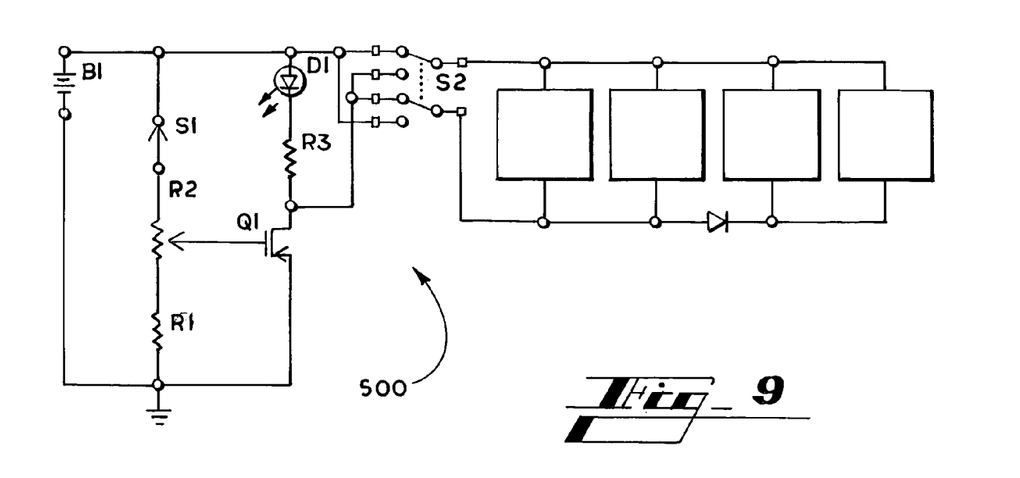
FIG. 9 illustrates a schematic diagram of another embodiment of a control circuit.

FIG. 9 illustrates a schematic diagram of another embodiment of a control circuit 500.

The circuit 500 is used to supply power to the alternate embodiment just described above. Battery B1 is the power source, which in a typical implementation is a lithium-ion battery. S1 is an on/off switch. Resistors R1 and R2 make up a voltage divider controlling gate voltage on Q1, which is typically a power MOSFET that controls the voltage to the Peltier chips. Resistor R3 and diode D1 are parallel to the output and indicate the output voltage intensity. Switch S2 changes the polarity if the output to select either hot or cold. Diode D2 prevents Peltier units 3 and 4 from operating while S2 is in the hot position.

With S1 on and S2 in the hot position, Q1 conducts. The intensity of the conduction is controlled by R2. The more Q1 conducts, the brighter D1 illuminate and the hotter Peltier chips 1 and 2 become. D2 prevents Peltier chips 3 and 4 from operating.

With S1 on and S2 in the cold position, the circuit 500 operates in the same way except that the polarity to the Peltier chips is reversed. Peltier chips 1 and 2 switch from hot to cold and Peltier chips 3 and 4 are energized and become cold. Peltier chips 3 and 4 are attached to the outer side of Peltier units 1 and 2 respectively. This orientation puts Peltier chips 3 and 4 on the now hot side of Peltier chips 1 and 2. This orientation is made in order to help dissipate the heat of Peltier units 1 and 2.

The above circuit diagram showed a battery in the circuit 400. The battery can be included in the temperature controller 135 in order to provide prolonged heating and cooling of the braces described above without the need for external power so that the user can remain independent and mobile. In a typical embodiment, the battery is rechargeable and can include a separate recharging unit that can be plugged in any standard circuit (in the home or automobile or by other suitable power sources) to recharge the battery. As such, the braces, the temperature controller, the battery and the battery charger can all be included in a self-contained heating and cooling orthopaedic brace system and kit.

It is appreciated that the above-described embodiments provide a secure brace that includes the further benefit of heating and cooling to the desired areas. The pad embodiments described above provide a unique heating and cooling element that delivers a desired temperature that is manually controlled and prolonged over time with the use of a battery. The use of thermally insulating material in the brace allows the temperature to be retained in the brace. In heating applications, the user's own body moisture is further retained in the brace to deliver moist heat that is often desired in therapeutic applications.

It is understood that many variations of the above-described braces are possible. For example, the temperature controllers are shown as having a toggle switch to switch between heating and cooling. In other embodiments, the braces and temperature controllers can be dedicated heating or cooling braces. In such an embodiment, the side of the pads facing the desired area of the body is simply a heating or cooling side, and the opposite side facing away from the user simply dissipates the undesired heating or cooling.

Therefore, the foregoing is considered as illustrative only of the principles of the invention. Further, various modifications may be made of the invention without departing from the scope thereof and it is desired, therefore, that only such limitations shall be placed thereon as are imposed by the prior art and which are set forth in the appended claims.

What is claimed is:

1. An orthopaedic brace temperature controlled apparatus, comprising:
   a temperature element that actively delivers heat and removes heat, the temperature element having a first surface and a second surface; and
   a thermally conductive sheet connected to the first surface and a thermally conductive sheet connected to the second surface,
   wherein one of the thermally conductive sheets is positioned adjacent an inner surface of the orthopaedic brace such that the other thermally conductive sheet is positioned adjacent a user's skin surface when the brace is donned; and
   a thermally insulating sheet, the temperature element being located within an aperture of the thermally insulating sheet, thereby leaving the first and second surfaces exposed for interconnection with the thermally conductive sheets.

2. The apparatus as claimed in claim 1 wherein the thermally insulating sheet is located between the thermally conductive sheet connected to the first surface and the thermally conductive sheet connected to the second surface such that the thermally conductive sheet located adjacent the inner surface of the orthopaedic brace is thermally isolated from the thermally conductive sheet located adjacent the user's skin when the brace is donned.

3. The apparatus as claimed in claim 1 further comprising thermal adhesive located between the first surface and the thermally conductive sheet and between the second surface and the thermally conductive sheet.

4. The apparatus as claimed in claim 1 further comprising a temperature controller connected to the temperature element.

5. The apparatus as claimed in claim 1 wherein the temperature element is a Peltier chip.

6. An orthopaedic brace, comprising:
   a main body having an outer surface, an inner surface and an opening;
   two elongated primary straps connected to one side of the main body, the primary straps being generally parallel to one another;
   a secondary strap connected to the end of each of the primary straps;
   buckles connected to the main body on the outer surface;
   a first set of primary strap fasteners being connected to the outer surface of the main body adjacent the opening;
   a second set of primary strap fasteners connected to the end of the primary straps adjacent the connection point of the primary straps and the secondary straps;
   a pocket connected to the inner surface of the main body adjacent the opening, the pocket having a front panel and a rear panel, the rear panel being connected to the inner surface of the main body; and
   a temperature pad located within the pocket, wherein the temperature pad maintains at least one of a heat level or a cold level for therapeutic orthopaedic treatment, the temperature pad comprising:
   a temperature element having a first surface and a second surface;
   a thermally conductive sheet connected to the first surface and a thermally conductive sheet connected to the second surface;
   a thermally insulating sheet located between the thermally conductive sheets, the temperature element being located within the thermally insulating sheet; and
   thermal adhesive located between the first surface and the thermally conductive sheet and between the second surface and the thermally conductive sheet.

7. The brace as claimed in claim 6 further comprising:
   a first set of secondary strap connectors located on a surface of each of the secondary straps; and
   a second set of secondary strap connectors located on the same surface and parallel to the first set of secondary strap connectors.

8. The brace as claimed in claim 6 wherein the front panel is mesh.

9. The brace as claimed in claim 6 further comprising a temperature controller connected to the temperature element.

10. The brace as claimed in claim 6 wherein the heat and cold levels are variable.

11. The brace as claimed in claim 6 wherein the heat and cold levels are constant.

* * * * *